(12) United States Patent
Koizumi et al.

(10) Patent No.: US 11,298,000 B2
(45) Date of Patent: Apr. 12, 2022

(54) ENDOSCOPIC DEVICE

(71) Applicant: Sony Olympus Medical Solutions Inc., Tokyo (JP)

(72) Inventors: Naoshi Koizumi, Kanagawa (JP); Noriaki Fujita, Tokyo (JP); Yuichi Yamada, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 299 days.

(21) Appl. No.: 16/137,013

(22) Filed: Sep. 20, 2018

(65) Prior Publication Data

US 2019/0125162 A1 May 2, 2019

(30) Foreign Application Priority Data

Nov. 2, 2017 (JP) .............................. JP2017-213243

(51) Int. Cl.
| | |
|---|---|
| *A61B 1/00* | (2006.01) |
| *A61B 1/045* | (2006.01) |
| *G02B 23/24* | (2006.01) |
| *A61B 5/107* | (2006.01) |

(52) U.S. Cl.
CPC ...... *A61B 1/00009* (2013.01); *A61B 1/00096* (2013.01); *A61B 1/00163* (2013.01); *A61B 1/00188* (2013.01); *A61B 1/045* (2013.01); *A61B 5/1079* (2013.01); *G02B 23/2446* (2013.01); *A61B 1/00043* (2013.01)

(58) Field of Classification Search
CPC ............ A61B 1/00009; A61B 1/00188; A61B 5/1079; A61B 1/1045; A61B 1/00163; A61B 1/00096; A61B 1/00043; A61B 5/6844; G02B 23/2446; G02B 23/2484
See application file for complete search history.

(56) References Cited

U.S. PATENT DOCUMENTS

| | | | | |
|---|---|---|---|---|
| 5,836,869 | A | * | 11/1998 | Kudo ...................... A61B 90/92 600/173 |
| 2011/0267444 | A1 | * | 11/2011 | Yamaguchi ............ H04N 7/183 348/65 |

FOREIGN PATENT DOCUMENTS

| | | | | |
|---|---|---|---|---|
| JP | 2006110055 | A | * 4/2006 | ............... A61B 1/04 |
| JP | 2006110055 | A | 4/2006 | |
| JP | 2011139760 | A | 7/2011 | |
| JP | 2015-134039 | | 7/2015 | |

* cited by examiner

*Primary Examiner* — Aaron B Fairchild
(74) *Attorney, Agent, or Firm* — Xsensus LLP

(57) ABSTRACT

An endoscopic device includes: an insertion portion configured to be inserted into a subject; an imaging unit configure to capture the subject image; a lens unit including a focus lens configured to adjust a focus by moving along an optical axis; a detection processor configured to perform detection processing of positioning a position of the focus lens at an in-focus position based on an image within the detection frame; a lens controller configured to position the focus lens at the in-focus position based on a processing result from the detection processor; a distal end detector configured to detect a distal end of a treatment tool in the captured image based on the captured image; and a detection frame setting unit configured to perform setting processing of setting a position of the detection frame in the captured image based on a position of the distal end of the treatment tool.

14 Claims, 15 Drawing Sheets

ENDOSCOPIC DEVICE

CROSS-REFERENCE TO RELATED APPLICATION

The present application claims priority to and incorporates by reference the entire contents of Japanese Patent Application No. 2017-213243 filed in Japan on Nov. 2, 2017.

BACKGROUND

The present disclosure relates to endoscopic devices.

Endoscopic devices for observing the inside of a subject (inside of a living body) such as a human have been known (e.g., see JP 2015-134039 A).

The endoscopic device described in JP 2015-134039 A includes an insertion portion that is to be inserted into a living body, and that has a distal end from which a subject image in the living body is captured, an imaging device that captures the subject image, a control device that processes a captured image captured by the imaging device to generate a video signal for display, and a display device that displays an image based on the video signal. In addition, the imaging device includes: a lens unit configured to move in an optical-axis direction; and a drive motor that moves the lens unit along the optical axis. Then, the endoscopic device described in JP 2015-134039 A can set the subject image in the captured image into focus (can make manual focusing possible) by changing a position (focus position) of the lens unit.

SUMMARY

Incidentally, a configuration as follows can be considered in the case of providing a so-called autofocus (AF) function in the endoscopic device described in JP 2015-134039 A.

That is, a detection frame is set on a part of region having a center position (hereinafter referred to as a central region) in a captured image. In addition, detection processing for positioning a focus position at an in-focus position is performed based on an image within the detection frame. A subject image within the detection frame is brought into focus at the in-focus position. Then, the focus position is positioned at the in-focus position based on a result of the detection processing.

A user such as a surgeon who performs surgery with the endoscopic device, however, sometimes wants to bring not the central region in the captured image but a region off the central region (hereinafter, region of interest) into focus. In such a case, the user needs to perform complicated work of changing an observation field by moving an insertion portion to position the region of interest at the center in the captured image (to position the region of interest within the detection frame). Unfortunately, this hinders improvements in convenience.

An endoscopic device according to one aspect of the present disclosure includes: an insertion portion configured to be inserted into a subject, and take in a subject image inside the subject from a distal end; an imaging unit configure to capture the subject image; a lens unit including a focus lens configured to adjust a focus by moving along an optical axis, the lens unit being configured to form the taken in subject image on the imaging unit; a detection processor configured to perform detection processing of positioning a position of the focus lens at an in-focus position where the subject image within a detection frame is brought into focus, based on an image within the detection frame, the detection frame being a part of region in a captured image captured by the imaging unit; a lens controller configured to position the focus lens at the in-focus position based on a processing result from the detection processor; a distal end detector configured to detect a distal end of a treatment tool included in the subject image in the captured image based on the captured image; and a detection frame setting unit configured to perform setting processing of setting a position of the detection frame in the captured image based on a position of the distal end of the treatment tool in the captured image.

DETAILED DESCRIPTION

Embodiments will now be described with reference to the drawings. The embodiments described below do not limit the disclosure. In addition, the same signs are attached to the same parts in the description of the drawings.

First Embodiment

Schematic Configuration of Endoscopic Device

Figure 1:
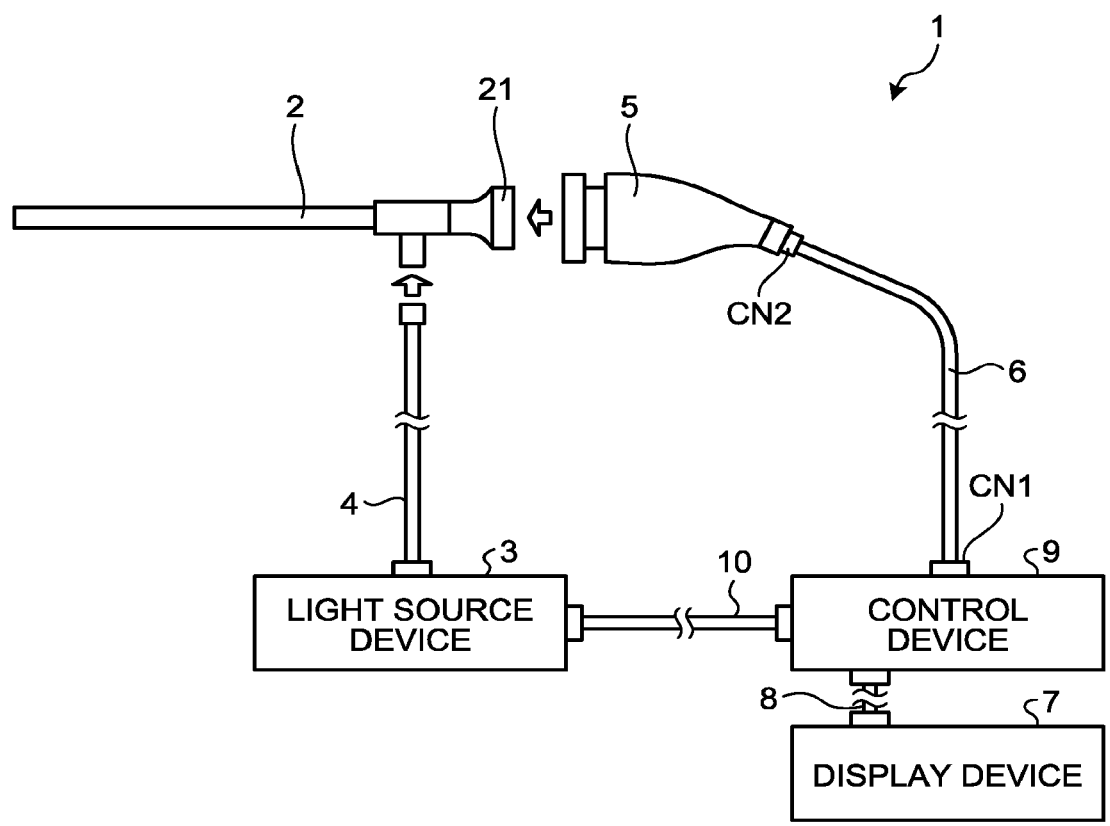
FIG. 1 is a diagram illustrating a schematic configuration of an endoscopic device according to a first embodiment.

FIG. 1 is a diagram illustrating a schematic configuration of an endoscopic device 1 according to a first embodiment.

The endoscopic device 1 is used in the medical field for observing the inside of a living body. As illustrated in FIG. 1, the endoscopic device 1 includes an insertion portion 2, a light source device 3, a light guide 4, a camera head 5, a first transmission cable 6, a display device 7, a second transmission cable 8, a control device 9, and a third transmission cable 10.

The insertion portion 2 includes a rigid endoscope. That is, the insertion portion 2 is rigid or at least partially flexible, has an elongated shape, e.g. is an insertion tube, and is to be inserted into a living body. An optical system including one or a plurality of lenses and configured to collect a subject image is provided in the insertion portion 2.

One end of the light guide 4 is connected to the light source device 3. The light source device 3 supplies light for illuminating the inside of the living body to the end of the light guide 4 under control of the control device 9.

One end of the light guide 4 is detachably connected to the light source device 3, and the other end is detachably connected to the insertion portion 2. Then, the light guide 4 transmits the light supplied from the light source device 3 from one end to the other end, and supplies the light to the insertion portion 2. The light supplied to the insertion portion 2 is emitted from a distal end of the insertion portion 2, and applied to the inside of the living body. Light applied to the inside of the living body and reflected in the living body (subject image) is collected by the optical system in the insertion portion 2.

The camera head 5 is detachably connected to a proximal end (an eyepiece portion 21 (FIG. 1)) of the insertion portion 2. Under control of the control device 9, the camera head 5 then captures the subject image collected by the insertion portion 2, and outputs an image signal (RAW signal) by the capturing. The image signal has, for example, 4K or more.

Note that the detailed configuration of the camera head 5 will be described later.

One end of the first transmission cable 6 is detachably connected to the control device 9 via a connector CN1 (FIG. 1), and the other end is detachably connected to the camera head 5 via a connector CN2 (FIG. 1). Then, the first transmission cable 6 transmits, for example, image signals output from the camera head 5 to the control device 9, and transmits, for example, control signals, synchronization signals, clocks, and power output from the control device 9 to the camera head 5, respectively.

Note that transmission of, for example, image signals from the camera head 5 to the control device 9 via the first transmission cable 6 may be performed by transmitting the image signals by optical signals or electric signals. This is applicable to transmission of the control signals, the synchronization signals, and the clocks from the control device 9 to the camera head 5 via the first transmission cable 6.

The display device 7 corresponds to a display unit according to the disclosure. The display device 7 includes a display with, for example, liquid crystal or organic electro luminescences (ELs), and displays a display image based on video signals from the control device 9 under control of the control device 9.

One end of the second transmission cable 8 is detachably connected to the display device 7, and the other end is detachably connected to the control device 9. Then the second transmission cable 8 transmits the video signals processed by the control device 9 and the control signals output from the control device 9 to the display device 7.

The control device 9 includes a central processing unit (CPU), and totally controls operations of the light source device 3, the camera head 5, and the display device 7.

Note that the detailed configuration of the control device 9 will be described later.

One end of the third transmission cable 10 is detachably connected to the light source device 3, and the other end is detachably connected to the control device 9. Then, the third transmission cable 10 transmits control signals from the control device 9 to the light source device 3.

Configuration of Camera Head

The configuration of the camera head 5 will now be described.

Figure 2:
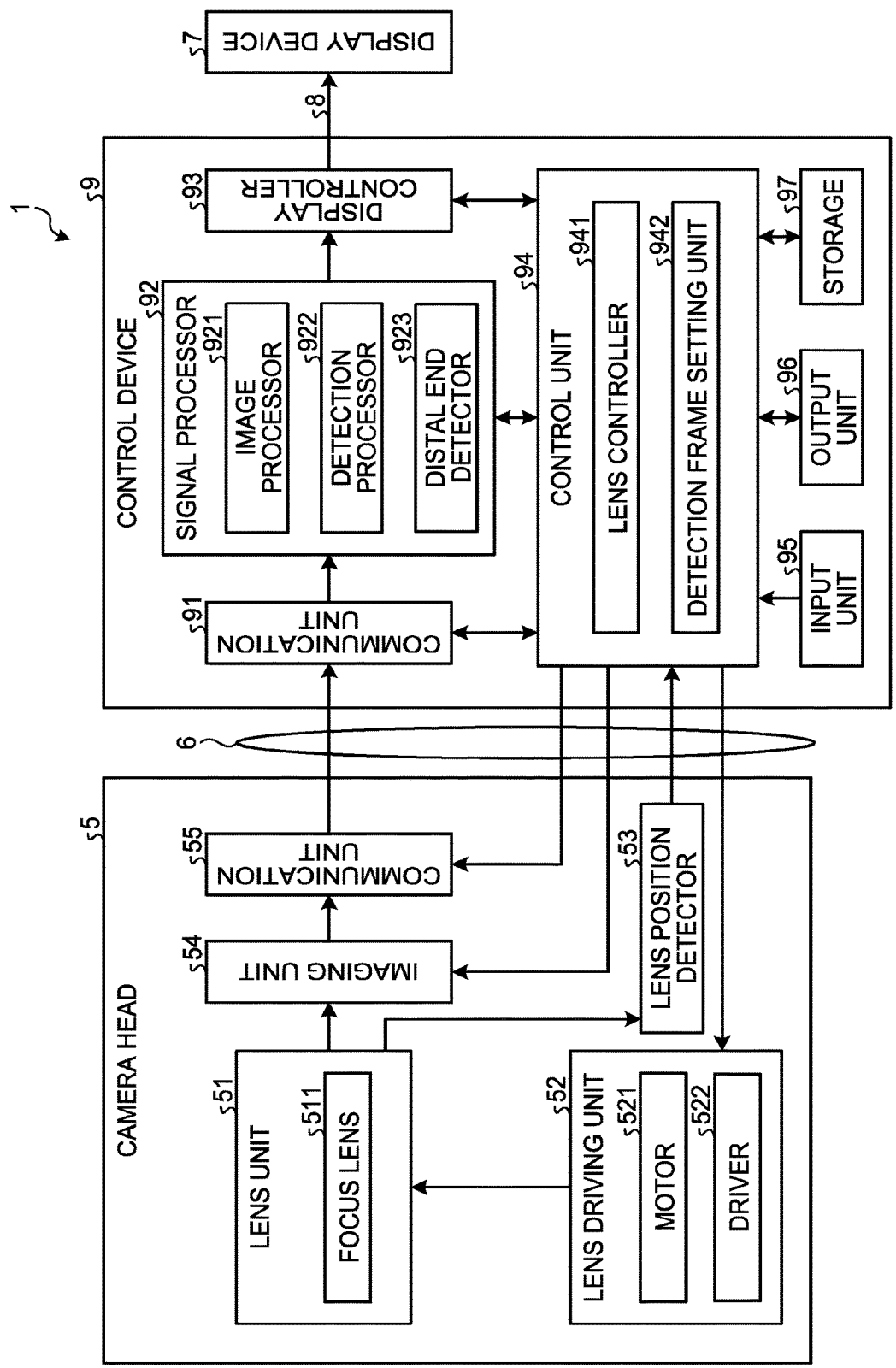
FIG. 2 is a block diagram illustrating configurations of a camera head and a control device.

FIG. 2 is a block diagram illustrating the configurations of the camera head 5 and the control device 9.

Note that, in FIG. 2, the connector CN1 between the control device 9 and the first transmission cable 6 and the connector CN2 between the camera head 5 and the first transmission cable 6 are not illustrated, and also a connector between the control device 9 and the second transmission cable 8 and a connector between the display device 7 and the second transmission cable 8 are not illustrated, for the purpose of illustration.

As illustrated in FIG. 2, the camera head 5 includes a lens unit 51, a lens driving unit 52, a lens position detector 53, an imaging unit 54, and a communication unit 55.

The lens unit 51 forms a subject image collected by the insertion portion 2 on an imaging surface of the imaging unit 54. As illustrated in FIG. 2, the lens unit 51 includes a focus lens 511.

The focus lens 511 includes one or a plurality of lenses, and adjusts a focus by moving along an optical axis.

In addition, a focus mechanism (not illustrated) for moving the focus lens 511 along the optical axis is provided in the lens unit 51.

As illustrated in FIG. 2, the lens driving unit 52 includes a motor 521 and a driver 522. The motor 521 drives the above-described focus mechanism. The driver 522 drives the motor 521. Then the lens driving unit 52 adjusts the focus of the lens unit 51 under control of the control device 9.

The lens position detector 53 includes a position sensor such as a photointerrupter, and detects a lens position (hereinafter referred to as a focus position) of the focus lens 511. Then, the lens position detector 53 outputs a detection signal in accordance with the focus position to the control device 9 via the first transmission cable 6.

The imaging unit 54 images the inside of a living body under control of the control device 9. The imaging unit 54 includes a sensor chip with, for example, an imaging element (not illustrated) and a signal processor (not illustrated) integrally formed. The imaging element such as a charge coupled device (CCD) and a complementary metal oxide semiconductor (CMOS) receives the subject image, which is collected by the insertion portion 2 and formed by the lens unit 51, and converts the subject image into electric signals. The signal processor performs signal processing (such as A/D conversion) on electric signals (analog signals) from the imaging element, and outputs the image signals. The imaging unit 54 outputs the image signals (digital signals) after the A/D conversion. Note that the above-described signal processor (not illustrated) may be separately provided without being integrally formed with the imaging element.

The communication unit 55 functions as a transmitter that transmits the image signals output from the imaging unit 54 to the control device 9 via the first transmission cable 6. For example, the communication unit 55 includes a high-speed serial interface that communicates image signals at a transmission rate of 1 Gbps or more with the control device 9 via the first transmission cable 6.

Configuration of Control Device

The configuration of the control device 9 will now be described with reference to FIG. 2.

As illustrated in FIG. 2, the control device 9 includes a communication unit 91, a signal processor 92, a display controller 93, a control unit 94, an input unit 95, an output unit 96, and a storage 97, e.g., a memory.

The communication unit 91 functions as a receiver that receives the image signals output from the camera head 5 (communication unit 55) via the first transmission cable 6. For example, the communication unit 91 includes a high-speed serial interface that communicates image signals at a transmission rate of 1 Gbps or more with the communication unit 55.

The signal processor 92 processes the image signal (RAW signal) output from the camera head 5 (communication unit 55) and received by the communication unit 91 under control of the control unit 94. As illustrated in FIG. 2, the signal processor 92 includes an image processor 921, a detection processor 922, and a distal end detector 923.

The image processor 921 performs RAW processing such as optical black subtraction processing and demosaic processing on the image signal (RAW signal) received by the communication unit 91, and converts the RAW signal (image signal) into an RGB signal (image signal). In addition, the image processor 921 performs RGB processing such as white balance, RGB gamma correction, and YC conversion (conversion of an RGB signal into a luminance signal and a color difference signal (Y and $C_B/C_R$ signals) on the RGB signal (image signal). Furthermore, the image processor 921 performs YC processing such as color difference correction and noise reduction on the Y and $C_B/C_R$ signals (image signals).

The detection processor 922 performs detection processing for autofocus (AF) processing on the image signals (Y and $C_B/C_R$ signals) processed by the image processor 921.

For example, the detection processor 922 detects the contrast and the frequency components of an image within a detection frame, which is a part of region of the entire captured image of one frame captured by the imaging unit 54, based on pixel information (luminance signal (Y signal)) of each pixel within the detection frame. Then, the detection processor 922 outputs detection information (the contrast and the frequency components) obtained by the detection to the control unit 94.

The distal end detector 923 performs distal end detecting processing of detecting a distal end of a treatment tool (treatment tool such as an electric knife to be inserted into a living body) contained in a subject image in the captured image based on the image signal processed by the image processor 921.

For example, the distal end detector 923 determines whether or not the subject image in the captured image contains the distal end of the treatment tool by a known approach such as pattern matching. Then, when the distal end detector 923 determines that the subject image in the captured image contains the distal end of the treatment tool, the distal end detector 923 outputs a detection signal indicating the position of the distal end of the treatment tool in the captured image to the control unit 94. On the other hand, when the distal end detector 923 determines that the subject image in the captured image does not contain the distal end of the treatment tool, the distal end detector 923 outputs a detection signal indicating the effect to the control unit 94.

The display controller 93 generates a video signal for display based on the image signals (Y and $C_B/C_R$ signals) processed by the image processor 921 under control of the control unit 94. Then, the display controller 93 outputs the video signal to the display device 7 via the second transmission cable 8.

The control unit 94 includes, for example, a CPU. The control unit 94 controls operations of the light source device 3, the camera head 5, and the display device 7, and controls operation of the entire control device 9 by outputting control signals via the first to third transmission cables 6, 8, and 10. As illustrated in FIG. 2, the control unit 94 includes a lens controller 941 and a detection frame setting unit 942.

The lens controller 941 operates the lens driving unit 52, and performs AF processing of adjusting the focus of the lens unit 51 (changing the focus position) based on a processing result (detection information) from the detection processor 922.

For example, the lens controller 941 performs the AF processing by a so-called hill-climbing method (contrast AF) as described below.

That is, the lens controller 941 calculates a focus evaluation value for evaluating an in-focus state of the subject image within the detection frame based on the detection information (the contrast and the frequency components) output from the detection processor 922. Here, the lens controller 941 defines the contrast detected by the detection processor 922 and the sum of high-frequency components among the frequency components detected by the detection processor 922 as the focus evaluation value. Note that a larger focus evaluation value indicates sharper focus achieved. Then, the lens controller 941 operates the lens driving unit 52, and sequentially calculates the focus evaluation values based on the detection information output from the detection processor 922 while changing the focus position. The lens controller 941 sequentially stores focus information, in which the focus position detected by the lens position detector 53 and the focus evaluation value in accordance with the focus position are associated with each other, in the storage 97. Then, the lens controller 941 calculates a peak position (focus position) at which the focus evaluation value reaches the maximum value based on a plural pieces of focus information stored in the storage 97. In addition, the lens controller 941 calculates a moving direction and a moving amount based on the peak position (focus position) and the focus position at the present time detected by the lens position detector 53. The moving direction is a direction (a direction to the near point or a direction to the far point) for moving the focus lens 511 from the focus position at the present time to the peak position (focus position). Then, the lens controller 941 outputs the control signal in accordance with the moving direction and the moving amount to the lens driving unit 52, and positions the focus lens 511 at the peak position (focus position). This brings the subject image within the detection frame into focus in the captured image.

Note that the above-described AF processing is not limited to contrast AF, and other methods (e.g., phase difference AF.) may be adopted.

When the distal end detector 923 determines that the subject image in the captured image contains the distal end of the treatment tool, the detection frame setting unit 942 performs setting processing of setting a position of the detection frame to be used in the detection processing around the position of the distal end of the treatment tool in the captured image detected by the distal end detector 923. In addition, when the distal end detector 923 determines that the subject image in the captured image does not contain the distal end of the treatment tool, the detection frame setting unit 942 sets the position of the detection frame to be used in the detection processing as a default position (e.g., center position in the captured image).

The input unit 95 includes an operation device such as a mouse, a keyboard, and a touch panel, and receives an operation by a user.

The output unit 96 includes a speaker and a printer, and outputs various kinds of information.

The storage 97 stores, for example, programs to be performed by the control unit 94 and information necessary for processing with the control unit 94.

Operation of Endoscopic Device

Operation of the above-described endoscopic device 1 will now be described.

Figure 3:
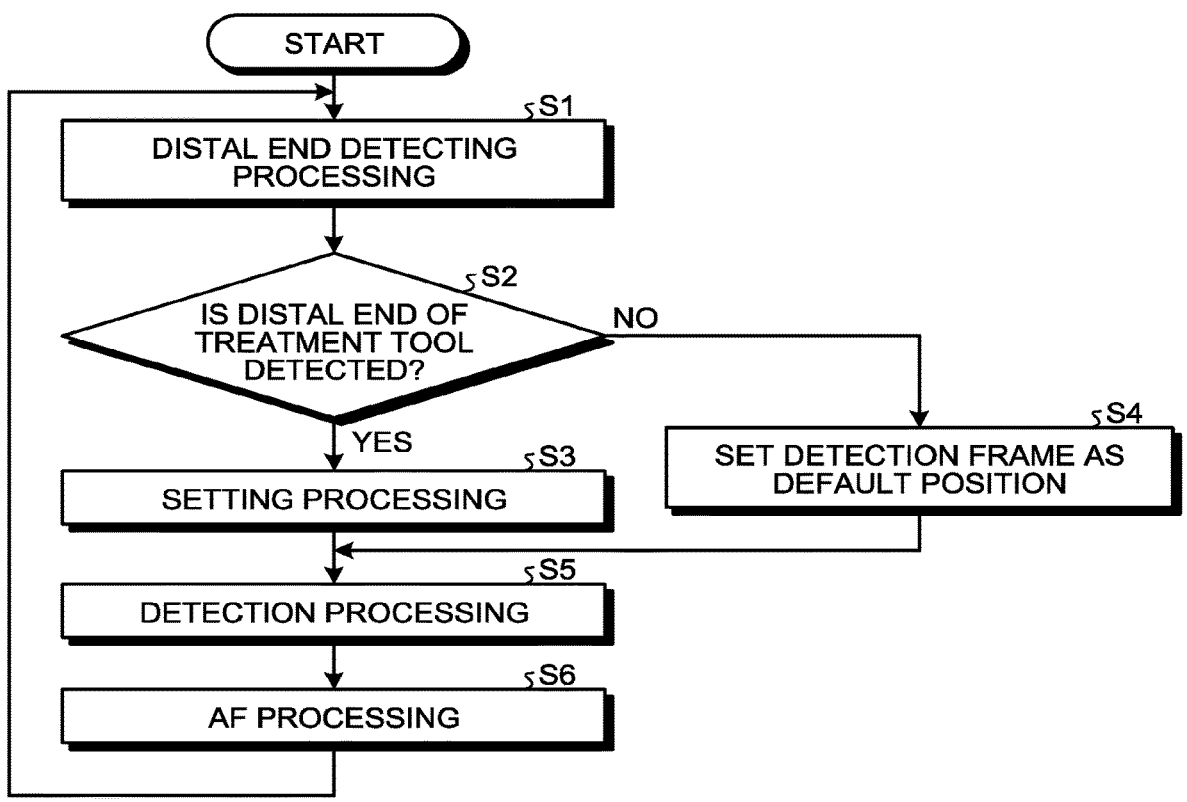
FIG. 3 is a flowchart illustrating operation of the endoscopic device.

FIG. 3 is a flowchart illustrating the operation of the endoscopic device 1.

First, the distal end detector 923 performs distal end detecting processing (Step S1).

After Step S1, when the distal end detector 923 determines that a subject image in a captured image contains a distal end of a treatment tool (Step S2: Yes), the detection frame setting unit 942 performs setting processing (Step S3). On the other hand, when the distal end detector 923 determines that the subject image in the captured image does not contain the distal end of the treatment tool (Step S2: No), the detection frame setting unit 942 sets a position of a detection frame to be used in the detection processing (Step S5) as a default position (Step S4).

After Step S3 or S4, the detection processor 922 performs detection processing based on pixel information (luminance signal (Y signal)) of each pixel within a detection frame set in Step S3 or S4 in the entire captured image (Step S5).

After Step S5, the lens controller 941 performs AF processing based on a processing result (detection information) from the detection processor 922 (Step S6). Then, the endoscopic device 1 proceeds to the processing of Step S1.

Figure 4A:
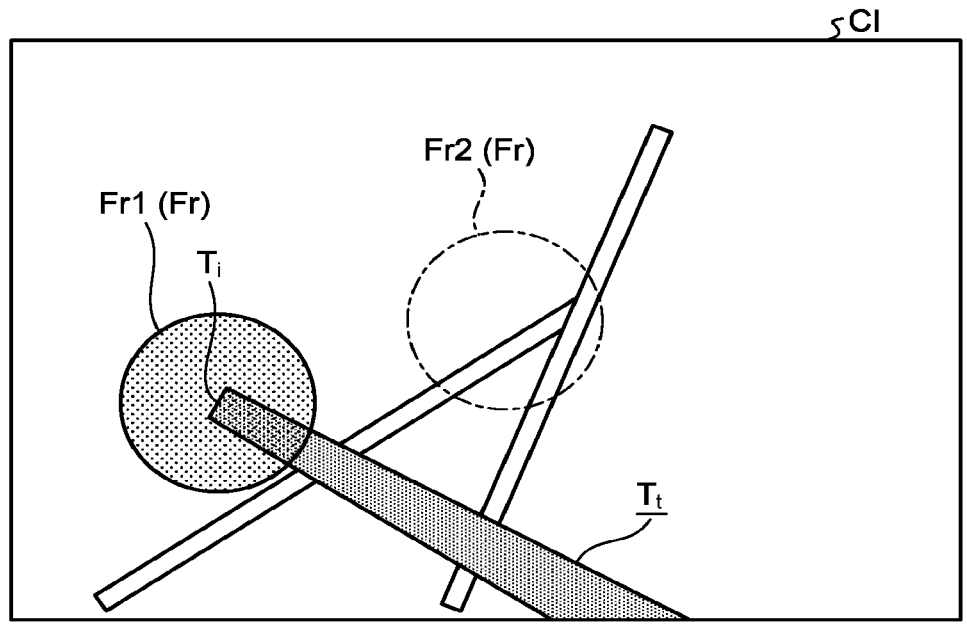
FIG. 4A illustrates one example of a detection frame to be set according to the operation of the endoscopic device illustrated in FIG. 3.
Figure 4B:
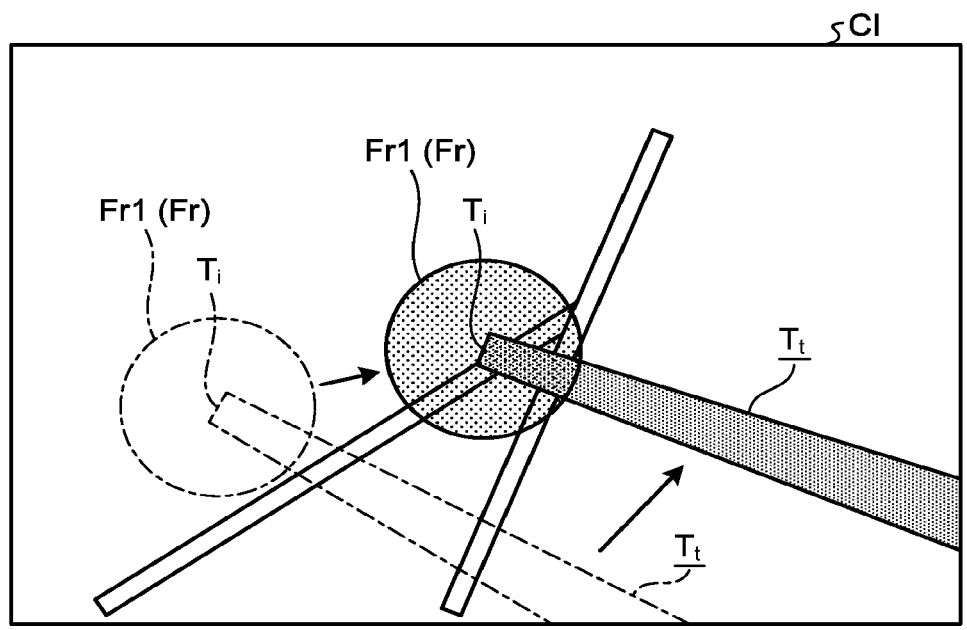
FIG. 4B illustrates one example of the detection frame to be set according to the operation of the endoscopic device illustrated in FIG. 3.

FIGS. 4A and 4B illustrate one example of a detection frame Fr to be set according to the operation of the endoscopic device 1 illustrated in FIG. 3.

When a subject image in a captured image CI contains a distal end $T_i$ of a treatment tool $T_t$ (Step S2: Yes), a detection frame Fr1 (Fr) is set around the position of the distal end $T_i$ in the captured image CI (Step S3) as illustrated by a solid line in FIG. 4A. Then, detection processing is performed within the detection frame Fr1 (Step S5), and the subject image within the detection frame Fr1 is brought into focus (Step S6).

On the other hand, when the subject image in the captured image CI does not contain the distal end $T_i$ of the treatment tool $T_t$ (Step S2: No), a detection frame Fr2 (Fr) is set at substantially a center position (default position) in the captured image CI as illustrated by a dashed dotted line in FIG. 4A (Step S4). Then, detection processing is performed within the detection frame Fr2 (Step S5), and the subject image within the detection frame Fr2 is brought into focus (Step S6).

In addition, as illustrated in FIGS. 4A and 4B, even in the case where the position of the treatment tool $T_t$ is changed, the detection frame Fr1 follows around the position of the distal end $T_i$ of the treatment tool $T_t$ in the captured image CI by repeatedly performing Steps S1 to S6.

Note that, in FIGS. 4A and 4B, the positions and the shapes (circular shapes) of the detection frames Fr1 and Fr2 are merely examples, and other positions and shapes may be adopted. That is, although, in FIG. 4A, the detection frame Fr1 is provided in a position (range) including the distal end $T_i$ of the treatment tool $T_t$, this is not limitative. The detection frame Fr1 may be provided in a position (range) not including the treatment tool $T_t$ as long as the position is around the position of the distal end $T_i$. This also applies to the following figures.

The above-described first embodiment provides an effect below.

The endoscopic device 1 according to the first embodiment detects the distal end $T_i$ of the treatment tool $T_t$ contained in the subject image in the captured image CI based on the captured image CI captured by the imaging unit 54. Then, the endoscopic device 1 sets the position of the detection frame Fr1 (Fr) in the captured image CI based on the position of the distal end $T_i$ of the treatment tool $T_t$ in the captured image CI.

Consequently, a user such as a surgeon who performs surgery with the endoscopic device 1 can set the detection frame Fr1 in a region, in the captured image CI, of interest desired to be brought into focus, and bring the region of interest into focus by moving the treatment tool $T_t$. That is, the treatment tool $T_t$ can be used as a pointer for setting a detection frame. Consequently, the endoscopic device 1 according to the first embodiment provides an effect of not requiring complicated work of changing an observation field by moving the insertion portion 2 to bring a region of interest into focus, and thus improving convenience.

Second Embodiment

A second embodiment will now be described.

In the following description, the same signs are attached to configurations similar to those of the above-described first embodiment, and a detailed description thereof will be omitted or simplified.

Figure 5:
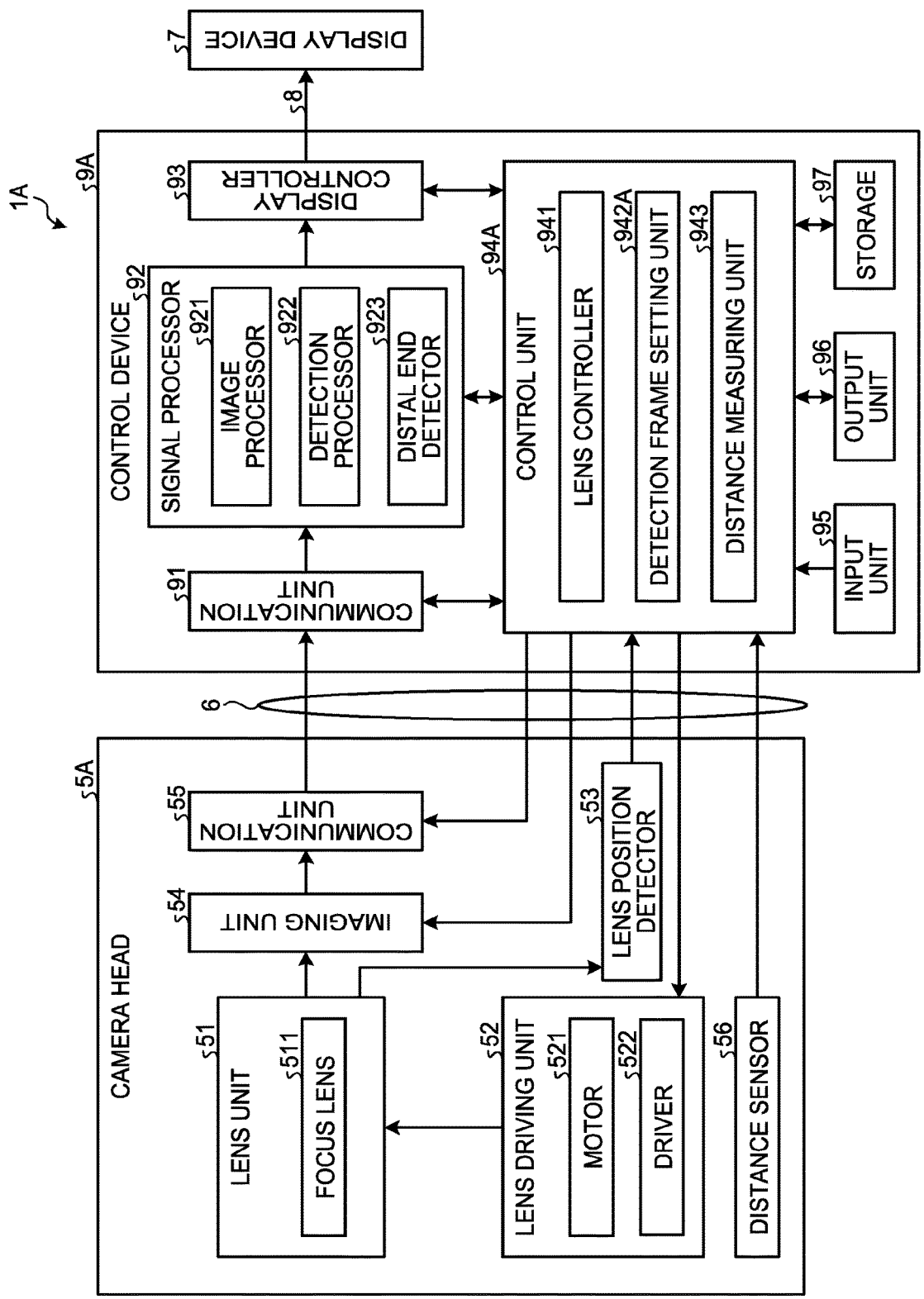
FIG. 5 is a block diagram illustrating a configuration of an endoscopic device according to a second embodiment.

FIG. 5 is a block diagram corresponding to FIG. 2, and illustrating a configuration of an endoscopic device 1A according to the second embodiment.

As illustrated in FIG. 5, the endoscopic device 1A according to the second embodiment adopts a camera head 5A and a control device 9A (control unit 94A) compared to the endoscopic device 1 (FIG. 2) described in the above first embodiment. The camera head 5A is obtained by adding a distance sensor 56 to the camera head 5. The control device 9A (control unit 94A) is obtained by adding a distance measuring unit 943 to the control device 9 (control unit 94).

The distance sensor 56 is used to measure a distance from a distal end $T_i$ of a treatment tool $T_t$ to a specific part in a living body. In the second embodiment, the distance sensor 56 includes a sensor module that measures the distance by a time of flight (TOF) method. That is, although not specifically illustrated, the distance sensor 56 includes a light source unit, a light receiver, and a signal processor. Light emitted from the light source unit is applied to the inside of the living body from a distal end of an insertion portion 2 via the insertion portion 2. Reflected light reflected in the living body is received by the light receiver via the insertion portion 2. Then, the signal processor generates a distance image indicating a distance to each position in the living body for each pixel based on electric signals output from the light receiver. The generated distance image is output to the control device 9A (control unit 94A) via a first transmission cable 6.

The distance measuring unit 943 measures the distance from the distal end $T_i$ of the treatment tool $T_t$ to the specific part in the living body based on the distance image output from the distance sensor 56.

In addition, as a result of providing the distance sensor 56 and the distance measuring unit 943 described above, a detection frame setting unit 942A according to the second embodiment differs, as described below, from the detection frame setting unit 942 described in the above first embodiment in timings at which pieces of processing (Steps S3 and S4) are performed.

Figure 6:
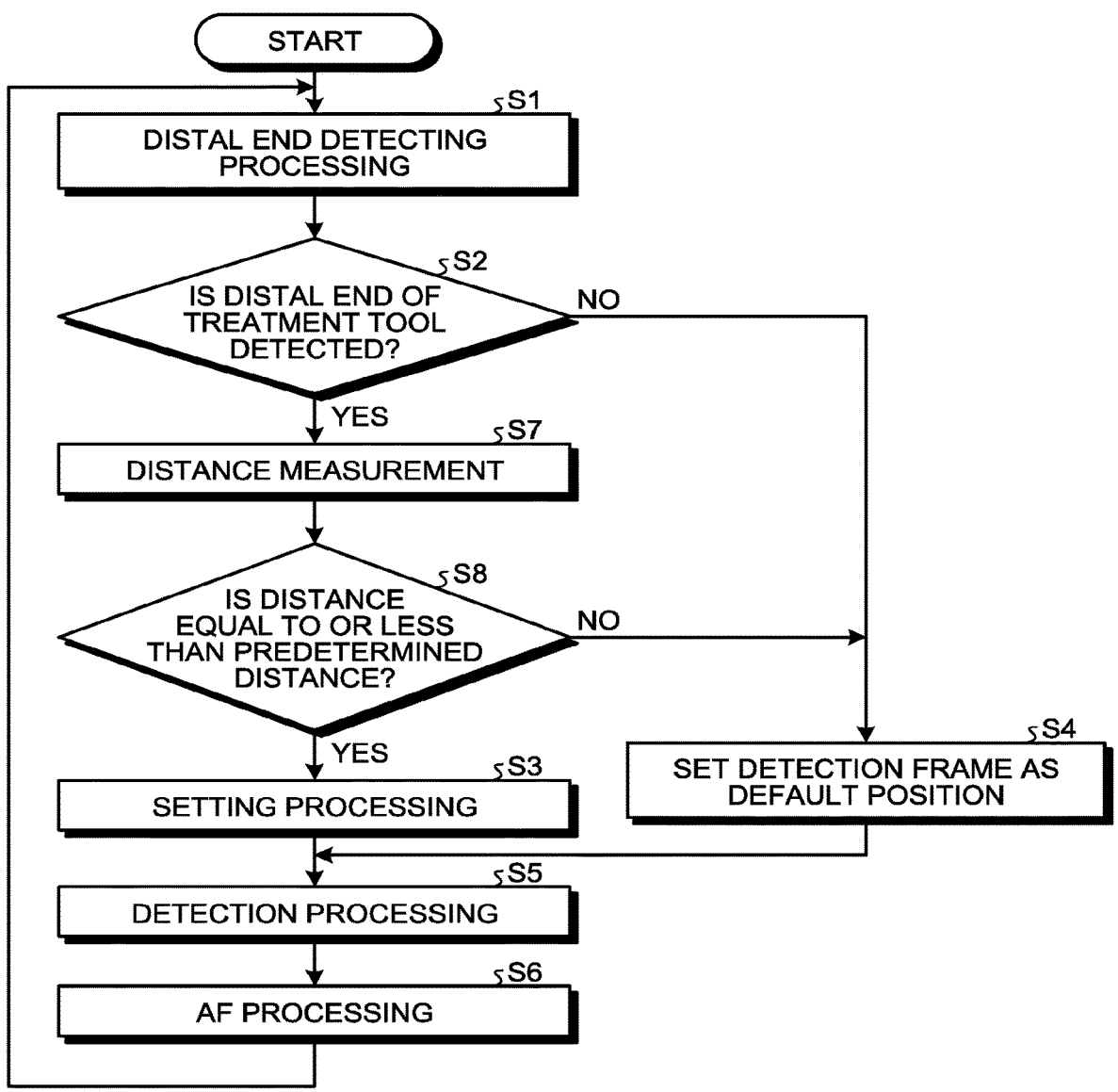
FIG. 6 is a flowchart illustrating operation of the endoscopic device.

FIG. 6 is a flowchart illustrating operation of the endoscopic device 1A.

As illustrate in FIG. 6, the operation of the endoscopic device 1A according to the second embodiment differs from the operation (FIG. 3) of the endoscopic device 1 described in the above first embodiment in that steps S7 and S8 are added. Steps S7 and S8 will thus be mainly described below.

Step S7 is performed when a distal end detector 923 determines that a subject image in a captured image CI contains the distal end $T_i$ of the treatment tool $T_t$ (Step S2: Yes). Specifically, in Step S7, the distance measuring unit 943 measures the distance from the distal end $T_i$ of the treatment tool $T_t$ to the specific part in the living body based on the distance image output from the distance sensor 56.

After Step S7, the detection frame setting unit 942A determines whether or not the distance measured in Step S7 is equal to or less than a predetermined distance (Step S8). Then, when the distance is determined to be equal to or less than the predetermined distance (Step S8: Yes), the detection frame setting unit 942A performs setting processing (Step S3). On the other hand, when the distance is determined to be more than the predetermined distance (Step S8: No), the detection frame setting unit 942A sets the position of a detection frame Fr2 (Fr) as a default position (Step S4).

Figure 7A:
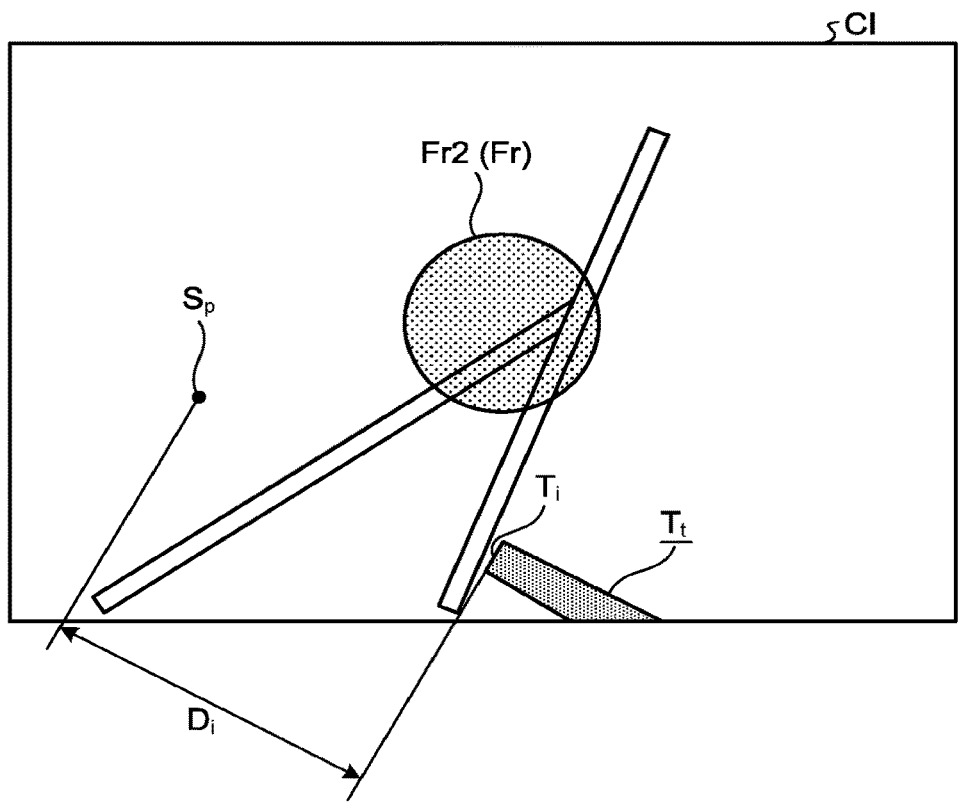
FIG. 7A illustrates one example of a detection frame to be set according to the operation of the endoscopic device illustrated in FIG. 6.
Figure 7B:
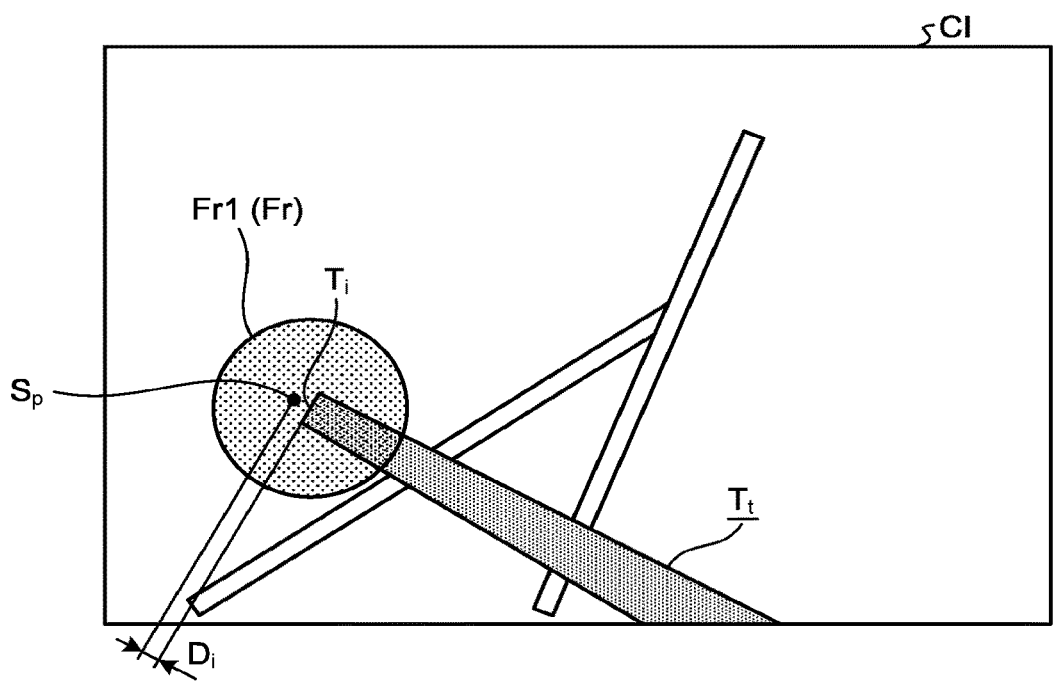
FIG. 7B illustrates one example of the detection frame to be set according to the operation of the endoscopic device illustrated in FIG. 6.

FIGS. 7A and 7B illustrate one example of the detection frame Fr to be set according to the operation of the endoscopic device 1A illustrated in FIG. 6.

When the subject image in the captured image CI contains the distal end $T_i$ of the treatment tool $T_t$ (Step S2: Yes), a distance $D_i$ from the distal end $T_i$ to a specific part $S_p$ in the living body is measured as illustrated in FIG. 7A or 7B (Step S7). Note that the specific part $S_p$ may be at a position optionally selected from a display image (captured image CI), which is displayed on a display device 7 in response to input operation to, for example, an operating unit (not illustrated) provided on an input unit 95 and the camera head 5A by a user, or at a predetermined position in the captured image CI.

Here, as illustrated in FIG. 7A, when the distance $D_i$ is more than the predetermined distance (Step S8: No), the detection frame Fr2 (Fr) is set at substantially a center position (default position) in the captured image CI (Step S4). On the other hand, as illustrated in FIG. 7B, when the distance $D_i$ is equal to or less than the predetermined distance (Step S8: Yes), a detection frame Fr1 (Fr) is set around the position of the distal end $T_i$ in the captured image CI (Step S3).

The above-described second embodiment provides an effect below in addition to an effect similar to that of the above-described first embodiment.

The endoscopic device 1A according to the second embodiment performs setting processing (Step S3) when the distance $D_i$ between the specific part $S_p$ in the captured image CI and the distal end $T_i$ of the treatment tool $T_t$ is equal to or less than the predetermined distance. This can avoid unnecessary follow-up of the detection frame Fr1 along with movement of the treatment tool $T_t$.

Third Embodiment

A third embodiment will now be described.

In the following description, the same signs are attached to configurations similar to those of the above-described first embodiment, and a detailed description thereof will be omitted or simplified.

Figure 8:
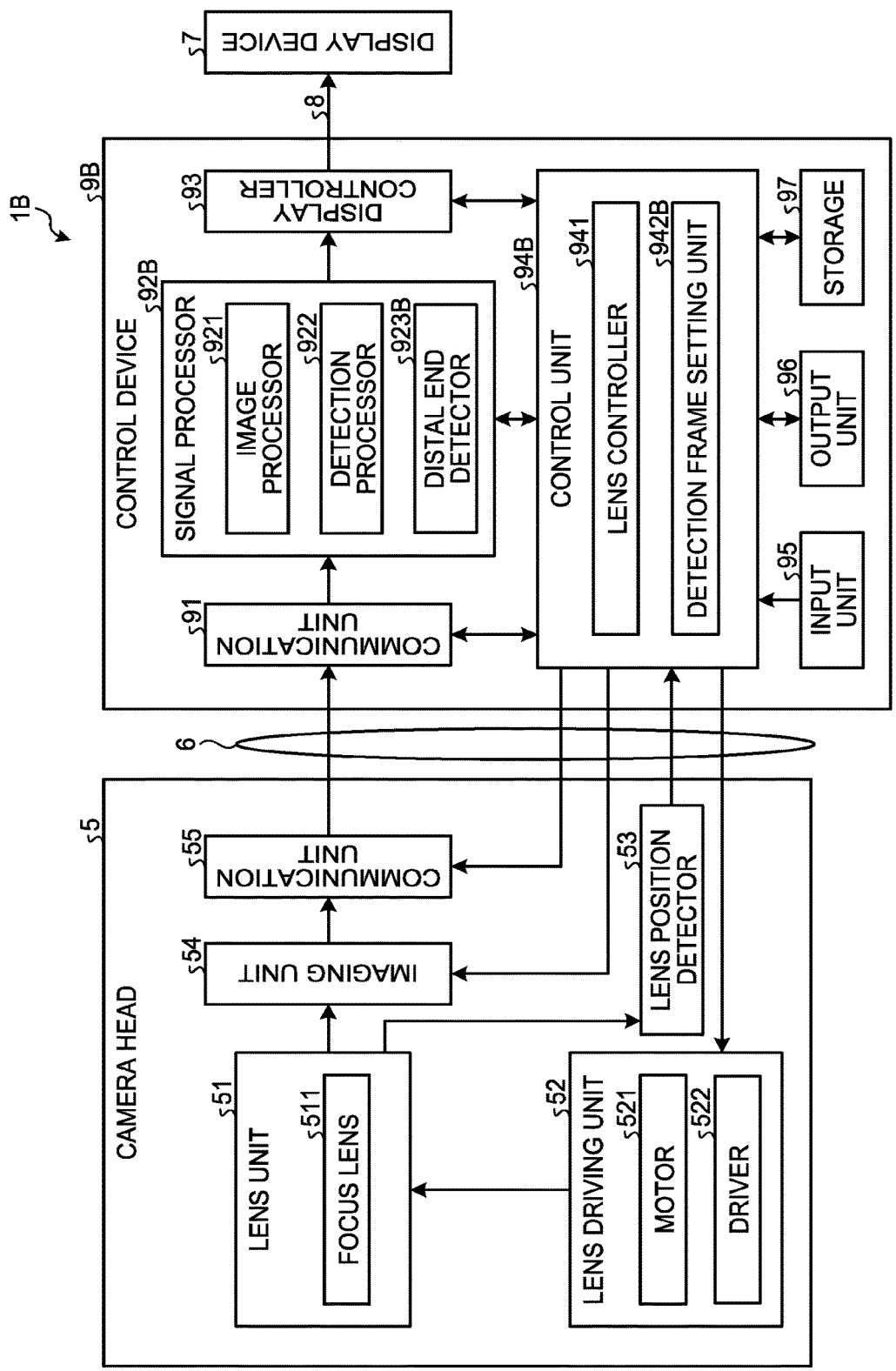
FIG. 8 is a block diagram illustrating a configuration of an endoscopic device according to a third embodiment.

FIG. 8 is a block diagram corresponding to FIG. 2, and illustrating a configuration of an endoscopic device 1B according to the third embodiment.

As illustrated in FIG. 8, the endoscopic device 1B according to the third embodiment adopts a control device 9B (signal processor 92B (distal end detector 923B)), which performs distal end detecting processing different from that performed by the distal end detector 923, compared to the endoscopic device 1 (FIG. 2) described in the above first embodiment.

The distal end detector 923B detects a distal end $T_i$ of a treatment tool $T_t$ contained in a subject image in a captured image CI, and also performs distal end detecting processing of determining the type of the treatment tool $T_t$.

Here, examples of the treatment tool $T_t$ include energy treatment tools (treatment tools for applying energy such as high-frequency energy, thermal energy, and ultrasonic energy to living tissues), grasping/peeling forceps, scissors forceps, staplers, puncture needles, baskets, snares, and drills. Then, the distal end detector 923B determines the type of the treatment tool $T_t$ on the captured image CI by using, for example, the type of the treatment tool $T_t$ as parameters. Note that, in the third embodiment, the energy treatment tool corresponds to a specific type of treatment tool according to the disclosure.

Then, when the distal end detector 923B determines that the subject image in the captured image CI contains the distal end $T_i$ of the treatment tool $T_t$ as a result of performing the distal end detecting processing, the distal end detector 923B outputs, to a control unit 94B, a detection signal indicating the type of the treatment tool $T_t$ together with a detection signal indicating the position of the distal end $T_i$ of the treatment tool $T_t$ in the captured image CI. On the other hand, when the distal end detector 923B determines that the subject image in the captured image CI does not contain the distal end $T_i$ of the treatment tool $T_t$, the distal end detector 923B outputs a detection signal indicating the effect to the control unit 94B.

In addition, as a result of changing the distal end detecting processing at the distal end detector 923B, a detection frame setting unit 942B (control unit 94B) according to the third embodiment differs, as described below, from the detection frame setting unit 942 described in the above first embodiment in timings at which pieces of processing (Steps S3 and S4) are performed.

Figure 9:
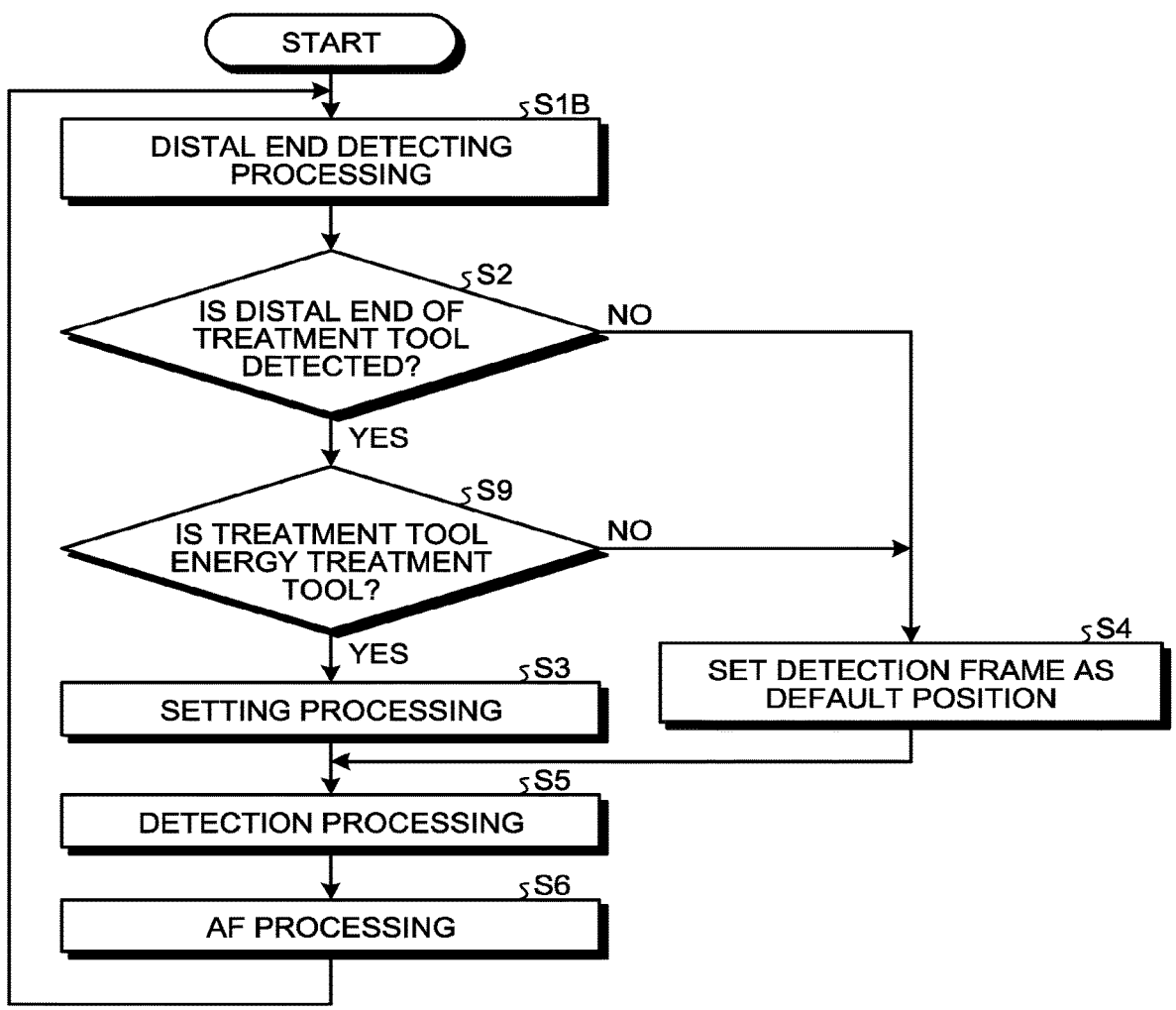
FIG. 9 is a flowchart illustrating operation of the endoscopic device.

FIG. 9 is a flowchart illustrating operation of the endoscopic device 1B.

As illustrate in FIG. 9, the operation of the endoscopic device 1B according to the third embodiment differs from the operation (FIG. 3) of the endoscopic device 1 described in the above first embodiment in that Step S1B is adopted instead of Step S1, and Step S9 is added. Steps S1B and S9 will thus be mainly described below.

First, the distal end detector 923B performs distal end detecting processing (Step S1B). Then, the endoscopic device 1B proceeds to the processing of Step S2.

Step S9 is performed when a distal end detector 923B determines that the subject image in the captured image CI contains the distal end $T_i$ of the treatment tool $T_t$ (Step S2: Yes). Specifically, when the distal end detector 923B determines that the treatment tool $T_t$ is an energy treatment tool (Step S9: Yes), the detection frame setting unit 942B performs setting processing (Step S3). On the other hand, when the distal end detector 923B determines that the treatment tool $T_t$ is not an energy treatment tool (Step S9: No), the detection frame setting unit 942B sets the position of a detection frame Fr2 (Fr) as a default position (Step S4).

The above-described third embodiment provides an effect below in addition to an effect similar to that of the above-described first embodiment.

Incidentally, for example, a grasping/peeling forceps (treatment tool) can be assumed to be used for grasping an unnecessary part that hinders observation of a region of interest desired to be brought into focus (desired to be observed (treated)) and keeping the unnecessary part away from the region of interest. In such use, if the detection frame Fr1 is regularly set around the position of a distal end of the grasping/peeling forceps, the unnecessary part grasped with the grasping/peeling forceps is brought into focus, and thus the region of interest is out of focus.

The endoscopic device 1B according to the third embodiment performs setting processing (Step S3) when the treatment tool $T_t$ is a specific type of treatment tool (energy treatment tool in the third embodiment). This enables the region of interest to be brought into focus without bringing the above-described unnecessary part into focus.

Fourth Embodiment

A fourth embodiment will now be described.

In the following description, the same signs are attached to configurations similar to those of the above-described first embodiment, and a detailed description thereof will be omitted or simplified.

Figure 10:
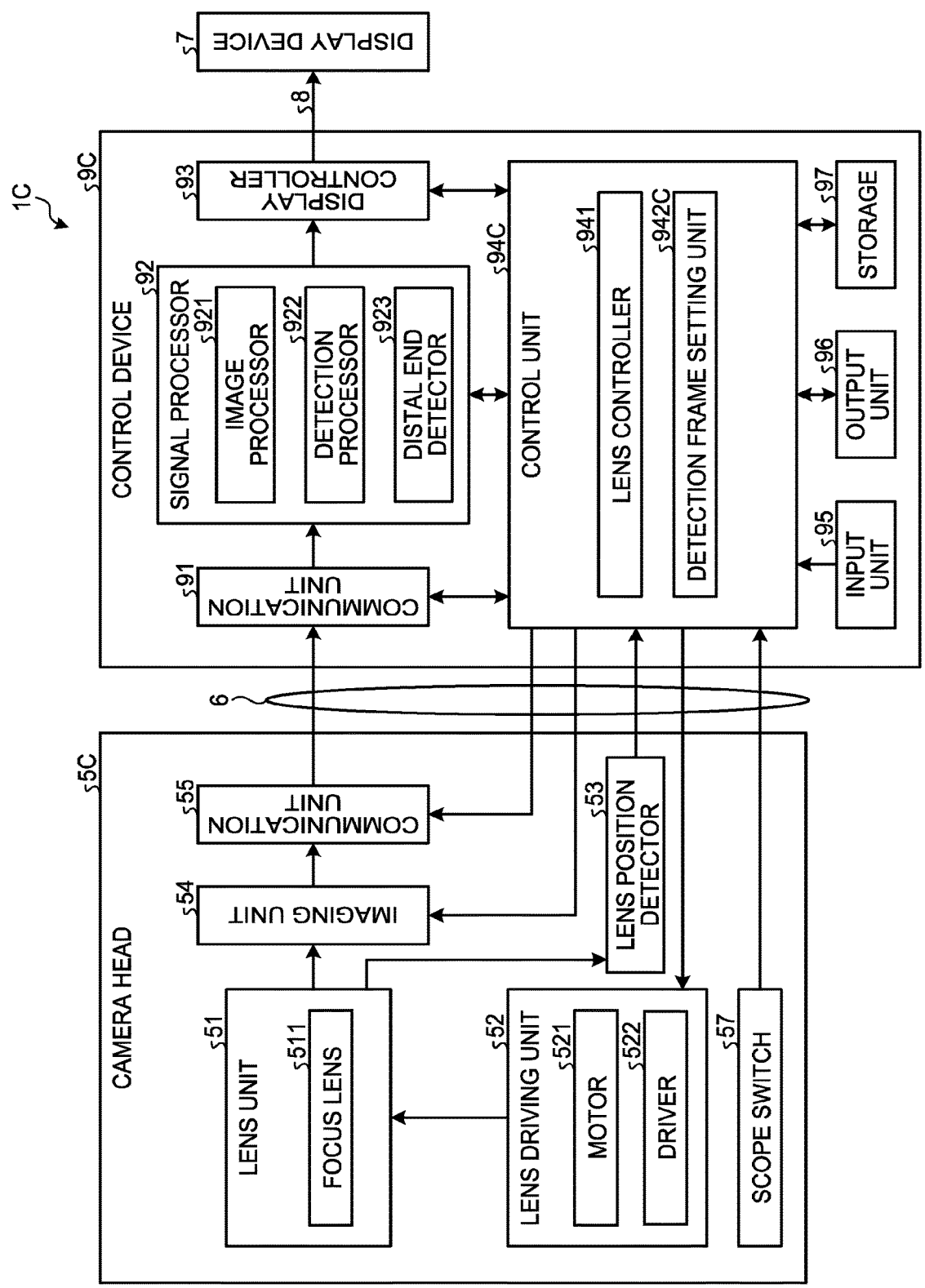
FIG. 10 is a block diagram illustrating a configuration of an endoscopic device according to a fourth embodiment.

FIG. 10 is a block diagram corresponding to FIG. 2, and illustrating a configuration of an endoscopic device 1C according to the fourth embodiment.

As illustrated in FIG. 10, the endoscopic device 1C according to the fourth embodiment adopts a camera head 5C compared to the endoscopic device 1 (FIG. 2) described in the above first embodiment. The camera head 5C is obtained by adding a scope switch 57 to the camera head 5.

The scope switch 57 corresponds to an operation input unit according to the disclosure. The scope switch 57 includes a push button switch provided on the camera head 5C, and outputs an operation signal in response to an operation by a user to a control device 9C (control unit 94C) via a first transmission cable 6.

In addition, as a result of providing the scope switch 57, a detection frame setting unit 942C (control unit 94C)) according to the fourth embodiment performs processing different from the processing executed by the detection frame setting unit 942 described in the above first embodiment, as described below.

Figure 11:
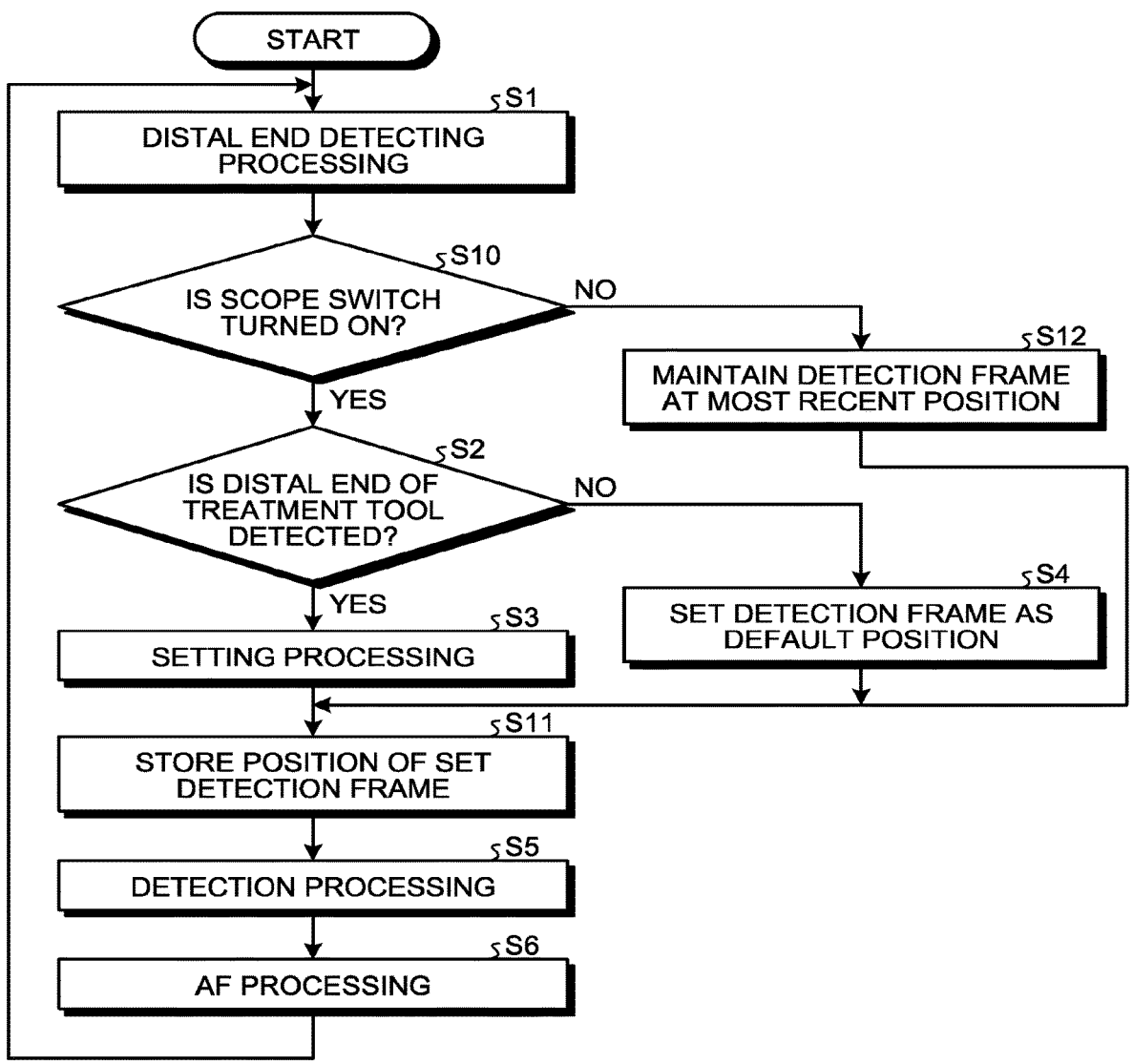
FIG. 11 is a flowchart illustrating operation of the endoscopic device.

FIG. 11 is a flowchart illustrating operation of the endoscopic device 1C.

As illustrate in FIG. 11, the operation of the endoscopic device 1C according to the fourth embodiment differs from the operation (FIG. 3) of the endoscopic device 1 described in the above first embodiment in that steps S10 to S12 are added. Steps S10 to S12 will thus be mainly described below.

Step S10 is performed after Step S1. Specifically, in Step S10, the detection frame setting unit 942C determines whether or not the scope switch 57 is turned ON (pushed down). When the scope switch 57 is determined to be turned ON (Step S10: Yes), the detection frame setting unit 942C proceeds to the processing of Step S2.

Step S11 is performed after Step S3, S4, or S12. Specifically, in Step S11, the detection frame setting unit 942C stores a position of a detection frame Fr set in Step S3, S4, or S12 in a storage 97. Note that the storage 97 corresponds to a position storing unit according to the disclosure. Then, the endoscopic device 1C proceeds to the processing of Step S5.

Step S12 is performed when the scope switch 57 is determined to be turned OFF (user operation for maintaining a position of a detection frame Fr1 is performed to the scope switch 57) (Step S10: No). Specifically, the detection frame setting unit 942C reads the position of the most recently set detection frame Fr stored in the storage 97 in Step S11, and sets the position of the detection frame Fr to be used in detection processing (Step S5) as a position of the read detection frame Fr.

Figure 12A:
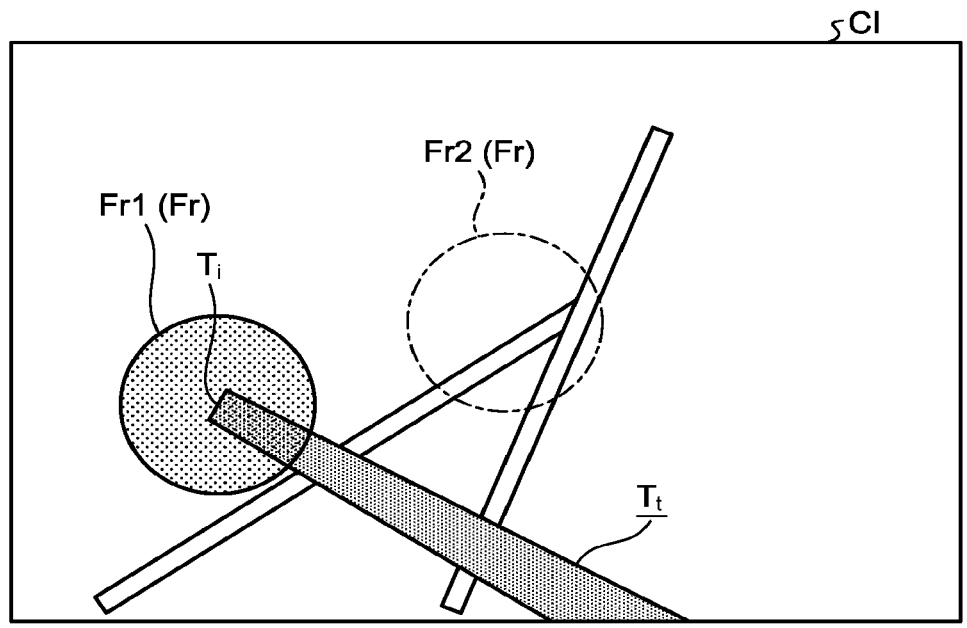
FIG. 12A illustrates one example of a detection frame to be set according to the operation of the endoscopic device illustrated in FIG. 11.
Figure 12B:
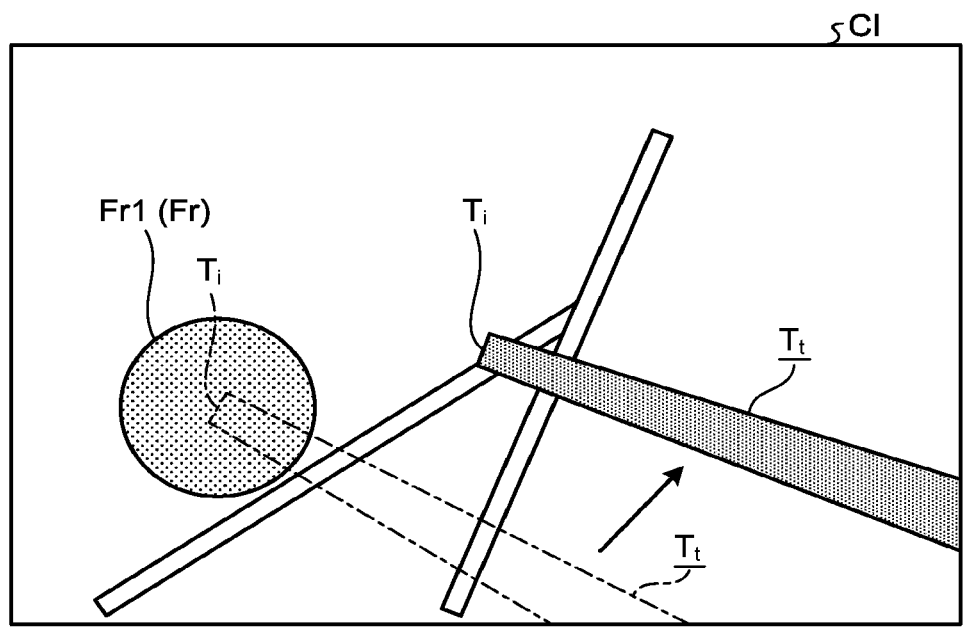
FIG. 12B illustrates one example of the detection frame to be set according to the operation of the endoscopic device illustrated in FIG. 11.

FIGS. 12A and 12B illustrate one example of the detection frame Fr to be set according to the operation of the endoscopic device 1 illustrated in FIG. 11.

As illustrated in FIG. 12A, when the scope switch 57 is turned on (step S10: Yes), the detection frame Fr (Fr1, Fr2) is set around a position of a distal end $T_i$ or at a default position in response to a result of detection (step S2) of the distal end $T_i$ of a treatment tool $T_t$ similarly to in the above-described first embodiment (steps S3 and S4). Then, the position of the detection frame Fr (Fr1, Fr2) is stored in the storage 97 (Step S11).

On the other hand, when the scope switch 57 is turned off in the next loop (Step S10: No) after the detection frame Fr1 is set around the position of the distal end $T_i$ (Step S3), the detection frame Fr1 is maintained at the most recent position (Step S12), as illustrated in FIG. 12B. That is, even in the case where the position of the treatment tool $T_t$ is changed, the detection frame Fr1 does not follow around the position of the distal end $T_i$ of the treatment tool $T_t$ in the captured image CI if the scope switch 57 is turned OFF.

The above-described fourth embodiment provides an effect below in addition to an effect similar to that of the above-described first embodiment.

When the endoscopic device 1C according to the fourth embodiment receives a user operation for maintaining the position of the detection frame Fr1, the endoscopic device 1C sets the position of the most recently set detection frame Fr1 stored in the storage 97 as a position of the detection frame in the captured image CI. This can avoid unnecessary follow-up of the detection frame Fr1 along with movement of the treatment tool $T_t$.

Fifth Embodiment

A fifth embodiment will now be described.

In the following description, the same signs are attached to configurations similar to those of the above-described first embodiment, and a detailed description thereof will be omitted or simplified.

Figure 13:
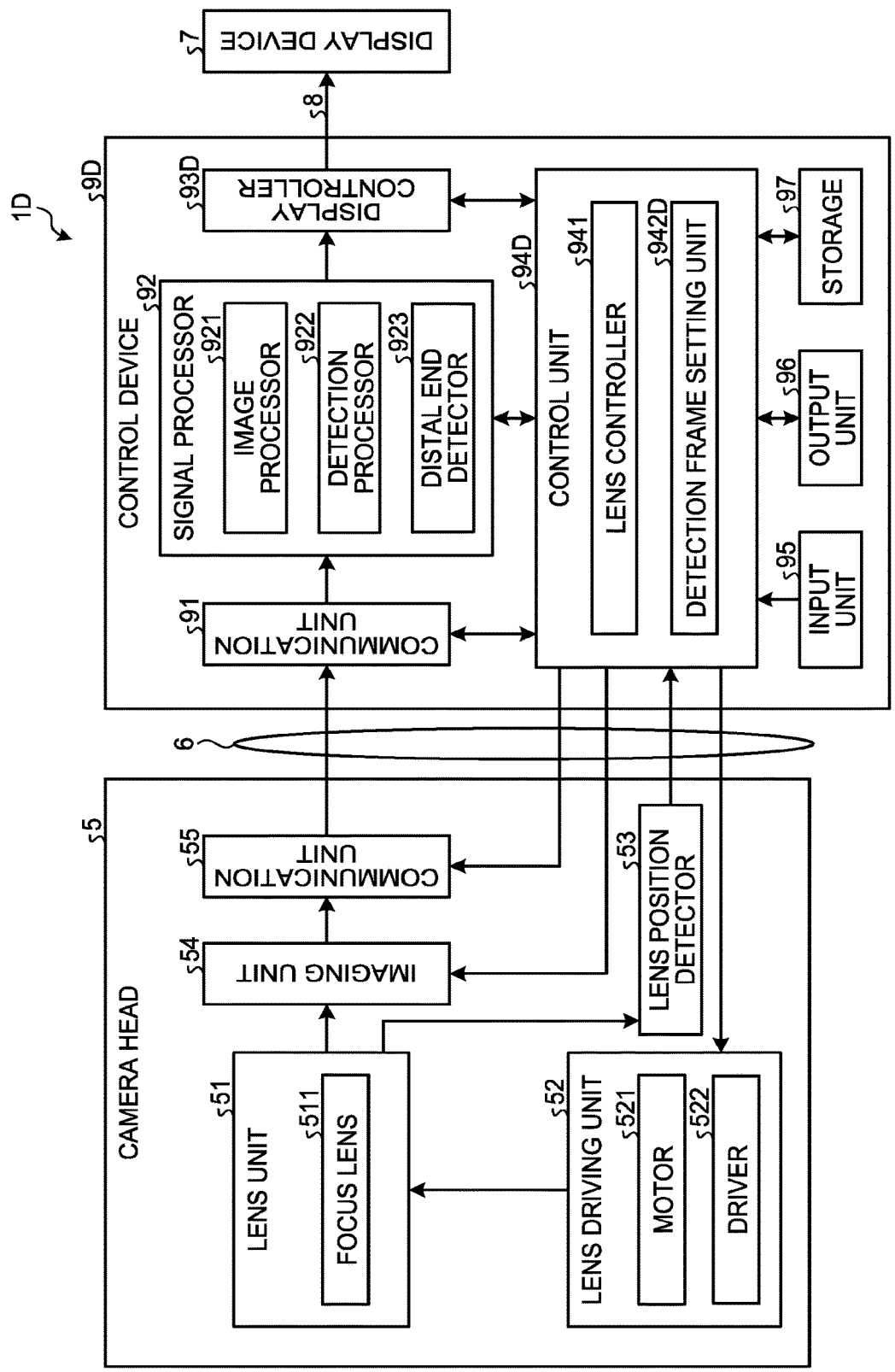
FIG. 13 is a block diagram illustrating a configuration of an endoscopic device according to a fifth embodiment.

FIG. 13 is a block diagram illustrating a configuration of an endoscopic device 1D according to the fifth embodiment, the figure corresponding to FIG. 2.

The endoscopic device 1D according to the fifth embodiment has a configuration that addresses a case where each distal end $T_i$ of a plurality of treatment tools $T_t$ is determined in a captured image CI, compared to the endoscopic device 1 described in the above first embodiment. That is, as illustrated in FIG. 13, the endoscopic device 1D (control device 9D (control unit 94D)) adopts a detection frame setting unit 942D instead of the detection frame setting unit 942 described in the above first embodiment, and adopts a display controller 93D instead of the display controller 93 described in the above first embodiment.

Figure 14:
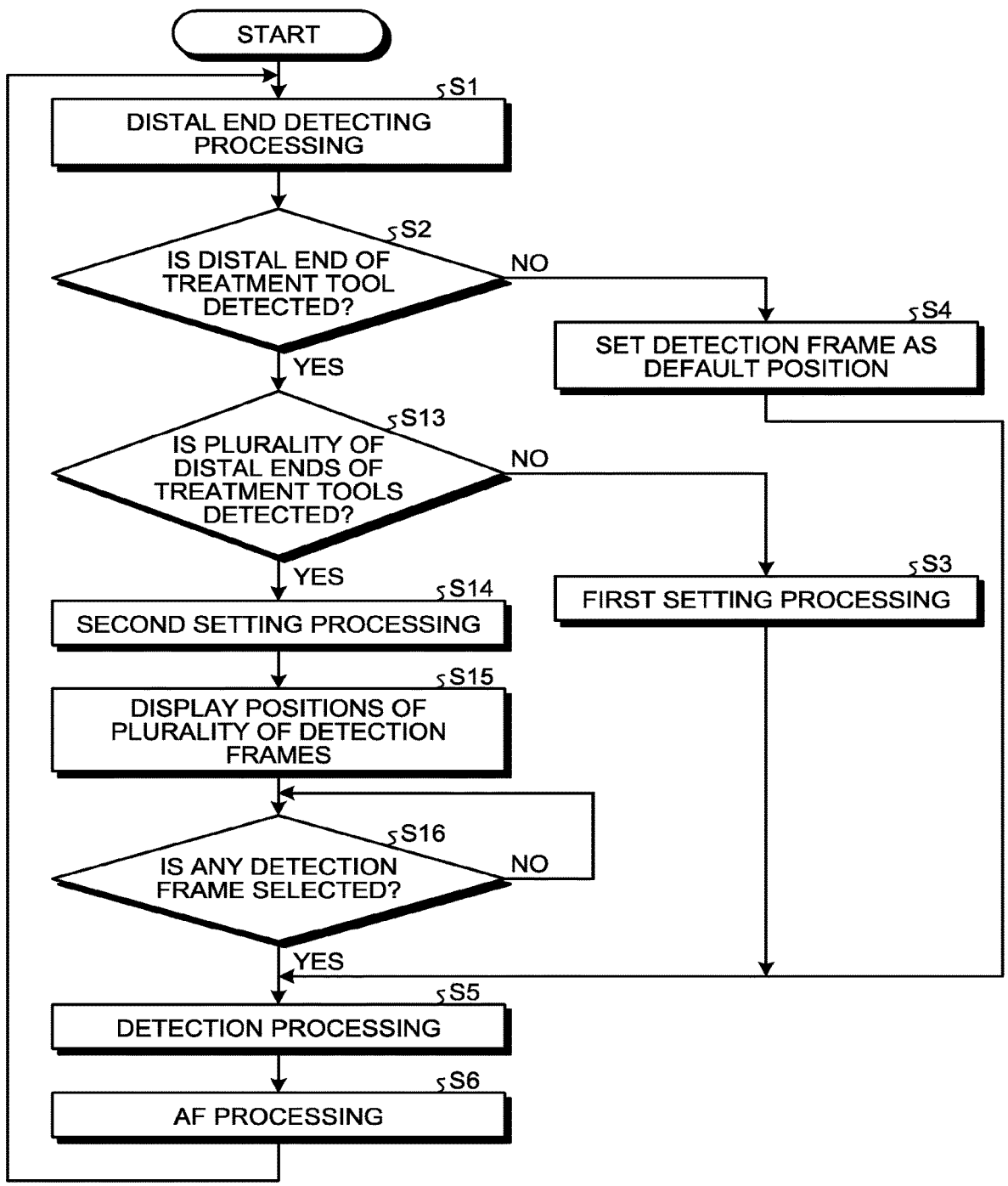
FIG. 14 is a flowchart illustrating operation of the endoscopic device.

FIG. 14 is a flowchart illustrating operation of the endoscopic device 1D.

As illustrate in FIG. 14, the operation of the endoscopic device 1D according to the fifth embodiment differs from the operation (FIG. 3) of the endoscopic device 1 described in the above first embodiment in that steps S13 to S16 are added. Steps S13 to S16 will thus be mainly described below.

Step S13 is performed when a distal end detector 923 determines that a subject image in a captured image CI contains the distal end $T_i$ of the treatment tool $T_t$ (Step S2: Yes). Specifically, when the distal end detector 923 determines that the plurality of distal ends $T_i$ of the treatment tools $T_t$ is not detected (Step S13: No), that is, only one distal end $T_i$ of the treatment tools $T_t$ is detected, the detection frame setting unit 942D performs setting processing similarly to in the above-described first embodiment (Step S3). On the other hand, when the distal end detector 923 determines that the plurality of distal ends $T_i$ of the treatment tools $T_t$ is detected (Step S13: Yes), the detection frame setting unit 942D sets each of the detection frames Fr1 around the positions of the plurality of distal ends $T_i$ (Step S14). Note that, to distinguish the pieces of setting processing in steps S3 and S14, the setting processing in Step S3 is described as "the first setting processing", and the setting processing in Step S14 is described as "the second setting processing" in FIG. 14.

After Step S14, the display controller 93D generates a video signal for display that enables identification, in the captured image CI, of the positions of the plurality of detection frames Fr1 set in Step S14 (Step S15). Then, the display device 7 displays a display image based on the video signal.

After Step S15, the control unit 94D constantly monitors whether or not any detection frame Fr1 (detection frame Fr1a in the example of FIG. 15) is selected from the plurality of detection frames Fr1 in the display image displayed in Step S14 in response to input operation by a user to, for example, an operating unit (not illustrated) provided on an input unit 95 and a camera head 5 (Step S16). Note that, the operating unit (not illustrated) provided on the input unit 95 and the camera head 5 corresponds to an operation input unit according to the disclosure.

Then, the detection processor 922 performs detection processing within a detection frame Fr1 set in Step S3, a detection frame Fr2 set in Step S4, or a detection frame Fr1 (detection frame Fr1a in the example of FIG. 15) selected in Step S16 (Step S5).

Figure 15:
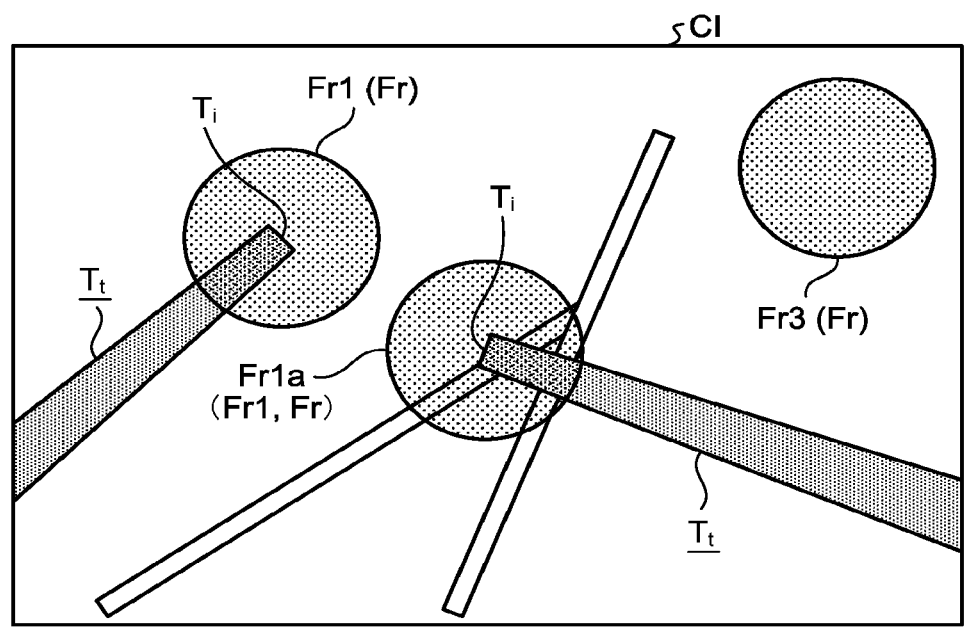
FIG. 15 illustrates one example of the detection frame to be set according to the operation of the endoscopic device illustrated in FIG. 14.

FIG. 15 illustrate one example of the detection frame Fr1 to be set according to the operation of the endoscopic device 1D illustrated in FIG. 14.

When the subject image in the captured image CI contains the distal ends $T_i$ of the plurality of treatment tools $T_t$ (Step S13: Yes), each of the detection frames Fr1 is set around the position of each of the distal ends $T_i$ as illustrated in FIG. 15. Then, the positions of the plurality of detection frames Fr1 are identifiably displayed on the display image on the display device 7 (Step S15).

Note that, in FIG. 15, the position of a detection frame Fr3 is identifiably displayed in addition to the positions of the above-described plurality of detection frames Fr1 in Step S15. Here, the position of the detection frame Fr3 corresponds to the position of the detection frame Fr1, which is set in the first setting processing (Step S3) or the second setting processing (Step S14) and stored in a storage 97 in a previous loop. In this case, the storage 97 corresponds to a position storing unit according to the disclosure. Then, when the position of the detection frame Fr3 is selected in Step S16, detection processing is performed in the detection frame Fr3 (Step S5).

The above-described fifth embodiment provides an effect below in addition to an effect similar to that of the above-described first embodiment.

The endoscopic device 1D according to the fifth embodiment detects the distal ends $T_i$ of the plurality of treatment tools $T_t$. When the positions of the plurality of detection frames Fr1 is set based on the positions of the plurality of distal ends $T_i$, the endoscopic device 1D identifiably displays the positions of the plurality of detection frames Fr1 on the display device 7 in the captured image CI. When a user operation for selecting the position of any detection frame Fr1a from the positions of the plurality of detection frames Fr1 displayed on the display device 7 is received, the endoscopic device 1D then performs the detection processing (Step S5) based on an image within the selected detection frame Fr1a.

Consequently, when surgery is performed with the endoscopic device 1D, a desired region of interest (subject image within the selected detection frame Fr1a) can be brought into focus even when the plurality of treatment tool $T_t$ is used.

In addition, the endoscopic device 1D according to the fifth embodiment identifiably displays the position of the detection frame Fr3 stored in the storage 97 on the display device 7 in the captured image CI. When a user operation for selecting the position of the detection frame Fr3 displayed on the display device 7 is received, the endoscopic device 1D then performs the detection processing (Step S5) based on an image within the detection frame Fr3.

Consequently, while surgery is performed with the endoscopic device 1D, a treatment is performed in advance, and then a region of concern (subject image within the detection frame Fr3) can be brought into focus again.

Other Embodiments

Although the embodiments have been described so far, the disclosure should not be limited only by the first to fifth embodiments described above.

In the above-described first to fifth embodiments, at least a part of structures provided in the camera heads 5, 5A, and 5C may be provided at a distal end in the insertion portion 2. In addition, the insertion portion 2 is not limited to a rigid endoscope, and may be a flexible endoscope.

In addition, in the above-described first to fifth embodiments, at least a part of structures provided in the control devices 9, 9A to 9D may be provided outside the control devices 9, 9A to 9D (e.g., on the camera heads 5, 5A and 5C, and connectors CN1 and CN2).

Although, in the above-described second embodiment, the distance $D_i$ between the specific part $S_p$ and the distal end $T_i$ of the treatment tool $T_t$ is measured by the TOF method, the measurement method is not limited to the TOF method. For example, a technique of measuring the distance $D_i$ by using a color filter and image processing (see, for example, JP 2017-40642 A) may be adopted, and the distance $D_i$ may be measured by using a parallax of a 3D camera.

Although, in the above-described third embodiment, a specific type treatment tool according to the disclosure is employed as an energy treatment tool, the specific type treatment tool is not limited to the energy treatment tool, and other treatment tools may be employed as the specific types of treatment tools.

Although, in the above-described fourth embodiment, the scope switch 57 is employed as an operation input unit, the operation input unit is not limited thereto. The operation input unit according to the disclosure may be provided at a section different from the camera head 5C as long as a user operation for maintaining the position of the detection frame Fr1 can be received. For example, the input unit 95 may be defined as the operation input unit according to the disclosure.

An endoscopic device according to the disclosure detects a distal end of a treatment tool contained in a subject image in a captured image based on the captured image captured by an imaging unit. Then, the endoscopic device sets the position of a detection frame in the captured image based on the position of the distal end of the treatment tool in the captured image.

Consequently, a user such as a surgeon who performs surgery with the endoscopic device can set the detection frame in a region of interest, in the captured image, desired to be brought into focus, and bring the region of interest into focus by moving the treatment tool. That is, the treatment tool can be used as a pointer for setting a detection frame. Consequently, the endoscopic device according to the disclosure provides an effect of not requiring complicated work of changing an observation field by moving an insertion portion to bring the region of interest into focus, and thus improving convenience.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. An endoscopic device comprising:
    an insertion tube configured to be inserted into a subject to collect a subject image inside the subject from a distal end;
    a sensor configured to capture the subject image;
    a focus lens configured to adjust a focus when moved along an optical axis, the focus lens to image the subject image on the sensor; and
    circuitry configured to:
    detect a distal end of a treatment tool included in the subject image in the captured image based on the captured image;
    on condition that the distal end of the treatment tool is detected, automatically set a first position of a detection frame in the captured image around a position of the distal end of the treatment tool in the captured image, otherwise, on condition that the distal end of the treatment tool is not detected, set a second position of the detection frame, the first position and the second position being offset from one another, wherein the detection frame is a part of the captured image;
    process an image within the detection frame;
    determine an in-focus position of the focus lens for the subject image within the detection frame, based on the processed image within the detection frame, and position the focus lens at the in-focus position while maintaining an observation field of the captured image.

2. The endoscopic device according to claim 1, wherein the circuitry is configured to measure a distance between a specific part in the subject and the distal end of the treatment tool,
    wherein, when the distance is equal to or less than a predetermined distance, the circuitry is configured to set a position of the detection frame as the first position and otherwise set the position of the detection frame as the second position.

3. The endoscopic device according to claim 1,
    wherein the circuitry is configured to determine a type of the treatment tool, and
    on condition that the treatment tool is a specific type of treatment tool, the circuitry is configured to set a position of the detection frame as the first position and otherwise set the position of the detection frame as the second position.

4. The endoscopic device according to claim 1, further comprising:
    an input configured to receive a user operation; and
    a memory to store the position of the detection frame,
    wherein, when the input receives a user input for maintaining the position of the detection frame, the circuitry is configured to set the position of most recently set detection frame stored in the memory as a position of the detection frame in the captured image.

5. The endoscopic device according to claim 1, further comprising:
    an input configured to receive a user operation; and
    a display to display an image wherein the circuitry is configured to
    display the captured image on the display,
    on condition that distal ends of a plurality of treatment tools are detected, and positions of a plurality of detection frames are set based on positions of the plurality of distal ends, identifiably display the positions of the plurality of detection frames in the captured image on the display, and
    when the input receives a user operation for selecting any of the positions of the plurality of detection frames displayed on the display, determine the focus position based on an image within the selected detection frame.

6. The endoscopic device according to claim 1, further comprising:
    an input configured to receive a user operation;
    a display to display an image; and
    a memory to store the position of the detection frame,
    wherein the circuitry is configured to
    display the captured image on the display, and
    identifiably displays the position of the detection frame stored in the memory in the captured image on the display, and
    when the input receives a user input for selecting the position of the detection frame displayed on the display, determine the focus position based on an image within the detection frame.

7. The endoscopic device according to claim 1, wherein the second position is a center position.

8. A medical observation device comprising:
    a sensor configured to capture a subject image;
    a focus lens configured to adjust a focus when moved along an optical axis, the focus lens to image the subject image on the sensor; and circuitry configured to:
detect a distal end of a treatment tool included in the subject image in the captured image based on the captured image;
on condition that the distal end of the treatment tool is detected, automatically set a first position of a detection frame in the captured image around a position of the distal end of the treatment tool in the captured image, otherwise, on condition that the distal end of the treatment tool is not detected, set a second position of the detection frame, the first position and the second position being offset from one another, wherein the detection frame is a part of the captured image;
process an image within the detection frame;
determine an in-focus position of the focus lens for the subject image within the detection frame, based on the processed image within the detection frame, and
position the focus lens at the in-focus position while maintaining an observation field of the captured image.

9. The medical observation device according to claim 8, wherein the circuitry is configured to measure a distance between a specific part in the subject and the distal end of the treatment tool,
wherein, when the distance is equal to or less than a predetermined distance, the circuitry is configured to set a position of the detection frame as the first position and otherwise set the position of the detection frame as the second position.

10. The medical observation device according to claim 8, wherein the circuitry is configured to determine a type of the treatment tool, and
on condition that the treatment tool is a specific type of treatment tool, the circuitry is configured to set a position of the detection frame as the first position and otherwise set the position of the detection frame as the second position.

11. The medical observation device according to claim 8, further comprising:
an input configured to receive a user operation; and
a memory to store the position of the detection frame,
wherein, when the input receives a user input for maintaining the position of the detection frame, the circuitry is configured to set the position of most recently set detection frame stored in the memory as a position of the detection frame in the captured image.

12. The medical observation device according to claim 8, further comprising:
an input configured to receive a user operation; and
a display to display an image wherein the circuitry is configured to
display the captured image on the display,
on condition that distal ends of a plurality of treatment tools are detected, and positions of a plurality of detection frames are set based on positions of the plurality of distal ends, identifiably display the positions of the plurality of detection frames in the captured image on the display, and
when the input receives a user operation for selecting any of the positions of the plurality of detection frames displayed on the display, determine the focus position based on an image within the selected detection frame.

13. The medical observation device according to claim 8, further comprising:
an input configured to receive a user operation
a display to display an image; and
a memory to store the position of the detection frame,
wherein the circuitry is configured to
display the captured image on the display, and
identifiably displays the position of the detection frame stored in the memory in the captured image on the display, and
when the input receives a user input for selecting the position of the detection frame displayed on the display, determine the focus position based on an image within the detection frame.

14. The medical observation device according to claim 8, wherein the second position is a center position.

* * * * *